US009738684B2

(12) United States Patent
Santosh et al.

(10) Patent No.: US 9,738,684 B2
(45) Date of Patent: Aug. 22, 2017

(54) N-TERMINALLY MODIFIED LINEAR AND BRANCHED POLYAMINE CONJUGATED PEPTIDOMIMETICS AS ANTIMICROBIALS AGENTS

(71) Applicant: COUNCIL OF SCIENTIFIC & INDUSTRIAL RESEARCH, New Delhi (IN)

(72) Inventors: Pasha Santosh, New Delhi (IN); Dewangan Rikeshwer Prasad, New Delhi (IN); Joshi Seema, New Delhi (IN)

(73) Assignee: COUNCIL OF SCIENTIFIC & INDUSTRIAL RESEARCH, New Dehli (IN)

( * ) Notice: Subject to any disclaimer, the term of this patent is extended or adjusted under 35 U.S.C. 154(b) by 0 days.

(21) Appl. No.: 14/754,002

(22) Filed: Jun. 29, 2015

(65) Prior Publication Data
US 2016/0376306 A1 Dec. 29, 2016

(51) Int. Cl.
*C07K 5/078* (2006.01)
*A61K 47/48* (2006.01)
*C07D 209/04* (2006.01)

(52) U.S. Cl.
CPC .... *C07K 5/06156* (2013.01); *A61K 47/48192* (2013.01); *C07D 209/04* (2013.01)

(58) Field of Classification Search
None
See application file for complete search history.

(56) References Cited

U.S. PATENT DOCUMENTS

| | | | |
|---|---|---|---|
| 5,192,756 | A | 3/1993 | Zasloff et al. |
| 5,744,453 | A | 4/1998 | Mintz et al. |
| 8,853,278 | B1 | 10/2014 | Looper et al. |
| 2006/0229252 | A1 | 10/2006 | Falla et al. |
| 2007/0197658 | A1 | 8/2007 | David et al. |
| 2011/0218168 | A1 | 9/2011 | Nelson et al. |

OTHER PUBLICATIONS

Dewangan, Antimicrobial Agents and Chemotherapy, Sep. 2014, vol. 58 No. 9, p. 5435-5447.*
Joshi, Org. Biomol. Chem., 2012, 10, 8326.*
Opar A. 2007. Bad bugs need more drugs. Nat. Rev. Drug Discov. 6:943-944, 2 pages.
Arias CA, Murray BE. 2009. Antibiotic-resistant bugs in the 21st century-a clinical super-challenge. N. Engl. J. Med. 360:439-443, 5 pages.
McKenna M. 2013. Antibiotic resistance: The last resort. Nature. 499:394-396, 3 pages.
Joo HS, Otto M. 2012. Molecular basis of in vivo biofilm formation by bacterial pathogens. Chem. Biol. 19:1503-1513, 21 pages.
Flemming HC, Wingender J. 2010. The biofilm matrix. Nat. Rev. Microbiol. 8:623-633, 11 pages.
Hoiby N, Bjarnsholt T, Givskov M, Molin S, Ciofu O. 2010. Antibiotic resistance of bacterial biofilms. Int. J. Antimicrob. Agents. 35:322-332, 11 pages.
Mah TC, O'Toole GA. 2001. Mechanisms of biofilm resistance to antimicrobial agents. Trends Microbiol. 9:34-39, 6 pages.
Hoffman LR, D'Argenio DA, MacCoss MJ, Zhang Z, Jones RA, Miller SI. 2005. Aminoglycoside antibiotics induce bacterial biofilm formation. Nature. 436:1171-1175, 5 pages.
Zasloff M. 2002. Antimicrobial peptides of multicellular organisms. Nature. 415:389-395, 7 pages.
Brogden KA. 2005. Antimicrobial peptides: pore formers or metabolic inhibitors in bacteria? Nat. Rev. Microbiol. 3:238-250, 13 pages.
Parisien A, Allain B, Zhang J, Mandeville R, Lan CQ. 2008. Novel alternatives to antibiotics: bacteriophages, bacterial cell wall hydrolases, and antimicrobial peptides. J. Appl. Microbiol. 104:1-13, 13 pages.
Mensa B, Howell GL, Scott R, DeGrado WF. 2014. Comparative mechanistic studies of brilacidin, daptomycin and the antimicrobial peptide LL16. Antimicrob. Agents Chemother. 58: 5136-5145, 10 pages.
Leszczynska K, Namiot A, Cruz K, Byfield FJ, Won E, Mendez G, Sokotowski W, Savage PB, Bucki R, Janmey PA. Potential of ceragenin CSA-13 and its mixture with pluronic F-127 as treatment of topical bacterial infections. 2011. J. Appl. Microbiol. 110:229-238, 10 pages.
Ooi N, Miller K, Hobbs J, Rhys-Williams W, Love W, Chopra I. 2009. XF-73, a novel antistaphylococcal membrane-active agent with rapid bactericidal activity. J. Antimicrob. Chemother. 64: 735-740, 6 pages.
Isaksson J, Brandsdal BO, Engqvist M, Flaten GE, Svendsen JSM, Stensen W. 2011. A synthetic antimicrobial peptidomimetic (LTX 109): stereochemical impact on membrane disruption. J. Med. Chem. 54:786-5795, 10 pages.
Igarashi K, Kashiwagi K. 2010. Modulation of cellular function by polyamines. Int. J. Biochem. Cell. Biol. 42:39-51, 13 pages.

(Continued)

*Primary Examiner* — Satyanarayana R Gudibande
(74) *Attorney, Agent, or Firm* — Colin P. Cahoon; Shaukat A. Karjeker; Carstens & Cahoon, LLP

(57) ABSTRACT

N-terminally modified linear and branched polyamine conjugated peptidomimetics as antimicrobials agents. The invention relates to therapeutically viable antibacterial compositions based on ultra short mimetic of host defense cationic peptides (HDCPs). The invention relates to template based N-terminal modified di-peptidomimetics with or without modifications in polyamine backbone as new antibacterial agents. Most active peptidomimetics were bactericidal and caused a rapid decrease in viability of broad range of Gram-positive and Gram-negative bacterial strains in low micromolar concentration range including activity against clinically relevant pathogen methicillin resistant *S. aureus* (MRSA) andmethicillin resistant *S. epidermidis* (MRSE). Further the peptidomimetics were effective against MRSA biofilms (formation inhibition/killing of preformed biofilms) in vitro and were non toxic to human red blood cells and peripheral blood mononuclear cells. The molecules described in present invention do not develop resistance against MRSA under in vitro conditions and hence may be used as topical agents or in similar applications.

10 Claims, 5 Drawing Sheets

(56) References Cited

OTHER PUBLICATIONS

Nowotarski SL, Woster PM, Casero RA Jr. 2013. Polyamines and cancer: implications for chemotherapy and chemoprevention. Expert Rev. Mol. Med. 22:15:e3, 28 pages.
Burns MR, Wood SJ, Miller KA, Nguyen T, Cromer Jr, David SA. 2005. Lysine-spermine conjugates: hydrophobic polyamine amides as potent lipopolysaccharide sequestrants. Bioorg. Med. Chem. 13:2523-2536, 14 pages.
Balakrishna R, Wood SJ, Nguyen TB, Miller KA, Suresh Kumar EV, Datta A, David SA. 2006. Structural correlates of antibacterial and membrane-permeabilizing activities in acylpolyamines. Antimicrob. Agents Chemother. 50:852-861, 10 pages.
Yingyongnarongkul BE, Apiratikul N, Aroonrerk N, Suksamrarn A. 2008. Synthesis of bis, tris and tetra(dihydrocaffeoyl) polyamine conjugates as antibacterial agents against VRSA. Arch. Pharm. Res. 31:698-704, 7 pages.
Kwon DH, Lu CD. 2007. Polyamine effects on antibiotic susceptibility in bacteria. Antimicrob. Agents Chemother. 51:2070-2077, 8 pages.
Joshi S, Dewangan RP, Yadav S, Rawat DS, Pasha S. 2012. Synthesis, antibacterial activity and mode of action of novel linoleic acid-dipeptide-spermidine conjugates. Org Biomol Chem. 10:8326-8335, 10 pages.
Dewangan RP, Joshi S, Kumari S, Gautam H, Yar MS, Pasha S. 2014. N-terminally modified linear and branched spermine backbone dipeptidomimetics against planktonic and sessile methicillin-resistant *Staphylococcus aureus*. Antimicrob Agents Chemother. 58:5435-5447, 13 pages.
Joshi GS, Spontak JS, Klapper DG, Richardson AR. 2011. Arginine catabolic mobile element encoded speG abrogates the unique hypersensitivity of *Staphylococcus aureus* to exogenous polyamines. Mol. Microbiol. 82:9-20, 12 pages.
Thurlow LR, Joshi GS, Clark JR, Spontak JS, Neely CJ, Maile R, Richardson AR. 2013. Functional modularity of the arginine catabolic mobile element contributes to the success of USA300 methicillin-resistant *Staphylococcus aureus*. Cell Host Microbe. 13:100-107, 16 pages.
Jahnsen RD, Frimodt-Moller N, Franzyk H. 2012. Antimicrobial activity of peptidomimetics against multidrug-resistant *Escherichia coli*: a comparative study of different backbones. J. Med. Chem. 55:7253-7261, 9 pages.
Thaker HD, Cankaya A, Scott RW, Tew GN. 2013. Role of amphiphilicity in the design of synthetic mimics of antimicrobial peptides with Gram-negative activity. ACS Med. Chem. Lett. 4:481-485, 5 pages.
Hansen T, Ausbacher D, Flaten GE, Havelkova M, Strøm MB. 2011. Synthesis of cationic antimicrobial β(2,2)-amino acid derivatives with potential for oral administration. J. Med. Chem. 54:858-68, 11 pages.
Hein-Kristensen L, Knapp KM, Franzyk H, Gram L. 2011. Bacterial membrane activity of α-peptide/β-peptoid chimeras: influence of amino acid composition and chain length on the activity against different bacterial strains. BMC Microbiol. 11:144, 12 pages.
Chhabra SR, Khan AN, Bycroft BW. 2000. Solid-phase synthesis of symmetrical and unsymmetrical polyamine analogues of philanthotoxins using a Dde-linker. Tetrahed. Lett. 41:1095-1098, 4 pages.
Kaiser E, Colescott RL, Bossinger CD, Cook PI. 1970. Color test for detection of free terminal amino groups in the solid-phase synthesis of peptides. Anal. Biochem. 34:595-598, 4 pages.
Wikler MA, Low DE, Cockerill FR, Sheehan DJ, Craig WA, Tenover FC, Dudley ML. 2006. Methods for dilution antimicrobial susceptibility tests for bacteria that grow aerobically—7th ed. Approved standard M7-A7. Clinical and Laboratory Standards Institute, Wayne, PA, 88 pages.
Yang ST, Lee JY, Kim HJ, Eu YJ, Shin SY, Hahm KS Kim JI. 2006. Contribution of a central proline in model amphipathic a helical peptides to self-association, interaction with phospholipids, and antimicrobial mode of action. FEBS J 273: 4040-4054, 15 pages.
Decker T, Lohmann-Mattthes ML. 1988. A quick and simple method for quantitation of lactate dehydrogenase release in measurement of cellular cytotoxicity and tumor necrosis factor (TNF) activity. J. Immunol. Methods 115:61-69, 9 pages.
Domadia PN, Bhunia A, Ramamoorthy A, Bhattacharjya S. 2010. Structure, interactions, and antibacterial activities of MSI-594 derived mutant peptide MSI-594F5A in lipopolysaccharide micelles: role of the helical hairpin conformation in outer-membrane permeabilization. J Am Chem Soc.132:18417-28, 12 pages.
Pearson D, Steigbigel RT, Davis HT, Chapman SW. 1980. Methods for reliable determination of minimal lethal antibiotic concentrations. Antimicrob. Agents Chemother. 18:699-708, 10 pages.
Singh M, Mukhopadhyay K. 2011. C-terminal amino acids of α-melanocyte-stimulating hormone are requisite for its antibacterial activity against *Staphylococcus aureus*. Antimicrob. Agents Chemother. 55:1920-1929, 10 pages.
Bauer J, Siala W, Tulkens PM, Van Bambeke F. 2013. A combined pharmacodynamic quantitative and qualitative model reveals the potent activity of daptomycin and delafloxacin against *Staphylococcus aureus* biofilms. Antimicrob. Agents Chemother. 57:2726-2737, 12 pages.
Nguyen LT, Chau JK, Perry NA, de Boer L, Zaat SA, Vogel HJ. 2010. Serum stabilities of short tryptophan- and arginine-rich antimicrobial peptide analogs. PLoS One. 5:e12684, 8 pages.
Chang, et al. "Fatty acid synthesis is a target for antibacterial activity of unsaturated fatty acids" FEBS Letters 579 (2005) 5157-5162 (6 pages).
Sun et al. "Antibacterial actions of fatty acids and monoglycerides against Helicobacter pylori" FEMS Immunology and Medical Microbiology 36 (2003) 9-17 (9 pages).
Hoiby et al. "Antibiotic resistance of bacterial biofilms" International Journal of Antimicrobial Agents 35 (2010) 322-332 (11 pages).
Wu et al. "Strategies for combating bacterial biofilm infections" International Journal of Oral Science (2014) 7, 1-7 (7 pages).
Greenway et al. "Mechanism of the Inhibitory Action of Linoleic Acid on the Growth of *Staphylococcus aureus*" Journal of General Microbiology (1979) 115, 233-245 (13 pages).

\* cited by examiner

N-TERMINALLY MODIFIED LINEAR AND BRANCHED POLYAMINE CONJUGATED PEPTIDOMIMETICS AS ANTIMICROBIALS AGENTS

FIELD OF THE INVENTION

The present invention relates to N-terminally modified linear and branched polyamine conjugated peptidomimetics as antimicrobials agents. Particularly, the invention relates to compositions comprising N-terminal modified linear/branched peptidomimetics conjugated with polyamines for treatment of infections caused by planktonic/biofilm embedded bacteria including multidrug resistant pathogens in human or animals.

BACKGROUND AND PRIOR ART OF THE INVENTION

The reference may be made to *Nat. Rev. Drug Discov.,* 6:943-944, 2007 discloses antibiotic resistance is a major global health care concern due to infections related to the escalating multiple drug resistant (MDR) pathogens.

The reference may be made to *N. Engl. J. Med.* 360:439-443, 2009 and *Nature,* 499:394- 396, 2013 disclose MDR strains of methicillin resistant *Staphylococcus aureus* (MRSA), vancomycin resistant *Enterrococci* (VRE) and carbapenem-resistant *Enterobacteriaceae* (CREs) in communities and nosocomial environments are rendering antibiotic therapy more difficult and costly at an unprecedented rate.

The reference may be made to *Nat. Rev. Microbiol,* 2:95-108, 2004 and *Chem. Biol.,* 19:1503-1513, 2012 disclose the development of resistance is aggravated by irrational use of antibiotics in livestock and healthcare practices that has armed microbes with multitude of novel drug resistance mechanisms. Microbes are among the most successful organisms owning to their rapid regeneration time which allows accumulation of resistance conferring genes through antibiotic stress or through exchange of plasmids with other microbes. Additionally a passive, known contributory life style approach towards resistance development in microbes is biofilm formation. Through a network of chemical signals (quorum sensing agents) biofilms nurture slow growing and heterogeneous microbial populations that differ among themselves phenotypically as well as genetically.

The reference may be made to *Nat. Rev. Microbiol.,* 8:623-633, 2010 discloses biofilms are matrix associated microbial communities adhered to surfaces or floating at air-water inter-phase where, the microbes are embedded in a self-produced exopolymeric substance (EPS). The biofilm matrix mostly comprises of proteins, extra cellular DNA with different extracellular polysaccharides.

The reference may be made to *Int. J. Antimicrob. Agents.,* 35:322-332, 2010 discloses the biofilms play a major role in almost 80% infections, including cystic fibrosis, dental plaques, chronic wounds and implanted medical device infections.

The reference may be made to *Trends Microbiol.,* 9:34-39, 2001 discloses most of the antibiotics target growth related metabolic processes in bacteria however, the heterogeneous population of actively dividing and persister microorganism in biofilms make them recalcitrant infection reservoirs which further contributes to virulence since the exopolymeric matrix and retarded metabolic activity inside biofilm communities leads to increased persistence of biofilms.

The reference may be made to *Nature.,* 436:1171-1175, 2005 discloses the bacteria in biofilms generally tolerate antibiotic treatment, and antibiotics can even produce a trigger for biofilm formation.

The reference may be made to *Nature,* 415:389-395, 2002 and *Nat. Rev. Microbiol.,* 3:238-250, 2005 describe, Host defense cationic peptides [HDCPs] (12-60 mer) and their mimics with several simultaneous target mechanisms in microbes are commercial candidates that hold potential to circumvent drug resistance MDR pathogens.

The reference may be made to *Nat. Rev. Microbiol.* 3:238-250, 2005 discloses HDCPs are evolutionary conserved and produced as a component of innate immunity by almost all living organisms as a first line of defense against invading microbes. Owing to global amphipathicity i.e. balance between positive charge at physiological pH and hydrophobicity, HDCPs predominantly exhibit membrane disruptive mode of action although they have also been reported as metabolic inhibitors in microbes.

The reference may be made to *J. Appl. Microbiol.,* 104: 1-13, 2008 describe the positive charge on HDCPs helps them to get attracted to negatively charged surface of bacterial cells, facilitating primary interactions. After initial attachment, by virtue of their amphipathic nature HDCPs are able to partition in bacterial membranes leading to transient or irreversible cellular content leakage which ultimately leads to bacterial cell death. Due to a rapid killing ability and simultaneous targeting of multiple organelles it is difficult for bacteria to develop resistance against HDCPs. HDCPs have also been reported to efficiently eradicate slow-growing cells from planktonic and biofilm cultures and thus have been proposed as promising alternative agents in the cure of biofilm associated MDR infections as well.

The reference may be made to *Nat. Biotechnol,* 17:755-757, 1999 describe the bottlenecks in the application of HDCPs have been their high cost, scalability, protease stability, reduced activity in presence of physiological salts concentrations and poor bioavailability.

The reference may be made to *Antimicrob. Agents Chemother.* 58: 5136-5145, 2014 and *J. Appl. Microbiol,* 110:229-238, 2011 and *J. Antimicrob. Chemother.* 64: 735-740, 2009 and *J. Med. Chem.* 54:786-5795, 2011 describe mimic HDCPs functions in miniature peptidomimetics has lead to discovery of potent molecules such as brilacidin, cationic steroid antibiotics (CSA), XF-73, and LTX-109 most of which are currently under clinical trials as antibacterial agents.

The reference may be made to *Int. J. Biochem. Cell. Biol.* 42:39-51, 2010 describes the polyamines (putrescine, spermidine, and spermine) are essential organic polycations that modulate cellular processes like nucleic acid packaging, DNA replication, transcription, and translation.

The reference may be made to *Expert Rev. Mol. Med.* 22:15:e3, 2013 and *Bioorg. Med. Chem.,* 13:2523-2536 and *Antimicrob. Agents Chemother.,* 50:852-861, 2006 describe the synthetic polyamine conjugates exhibit versatile biological activities, including anticancer, antiparasitic, antiendotoxin, and antibacterial activities.

The reference may be made to *J. Appl. Microbiol.,* 110: 229-238, 2011 and *Bioorg. Med. Chem.,* 13:2523-2536, 2005 and *Arch. Pharm. Res.* 31:698-704, 2008 disclose the role of polyamine conjugation in improving activity for a number of synthetic antibacterial agents, such as ceragenins, acylpolyamines, and caffeoyl polyamines.

The reference may be made to *Antimicrob. Agents Chemother.,* 51:2070-2077, 2007 describe the synergistic effect of exogenous polyamines and various antibiotics.

The reference may be made to *Org Biomol Chem.*, 10:8326-8335, 2012 and *Antimicrob Agents Chemother.*, 58:5435-5447, 2014 describe the ultra short di-peptidomimetics based on polyamine backbone that showed excellent anti methicillin resistant *S. aureus*(MRSA) activity in vitro against planktonic cells. Further, the designed di-peptidomimetics (*Org Biomol Chem.*, 10:8326-8335, 2012) were found equally or rather better active against methicillin resistant *S. aureus* as compared to *S. aureus*. Polyamines were initially thought to be ubiquitous and were expected to be present in mammals as well microbes, However, recently it was shown that *S. aureus* produces no spermine/spermidine or their precursors; therefore, polyamines and their conjugates act as toxins to *S. aureus*. [*Mol. Microbiol.* 82:9-20, 2011]

The reference may be made to *Cell Host Microbe*, 13:100-107, 2013 discloses Further, the exceptional virulence of MRSA strain USA300 was ascribed to development of resistance genes to spermidine and other polyamines.

Therefore, for polyamine-sensitive MRSA, conjugation of spermine is a robust strategy to overcome this deadly strain.

OBJECTIVE OF THE INVENTION

The main object of the present invention is to provide N-terminally modified linear and branched polyamine conjugated peptidomimetics as antimicrobials agents.

The other objective of the present invention is to provide the treatment of infections caused by planktonic/biofilm embedded bacteria including multidrug resistant pathogens in human or animals.

SUMMARY OF THE INVENTION

Accordingly, the present invention provides N-terminally modified linear and branched polyamine conjugated peptidomimetics as antimicrobials agents.

DETAILED DESCRIPTION OF THE INVENTION

Figure 1:
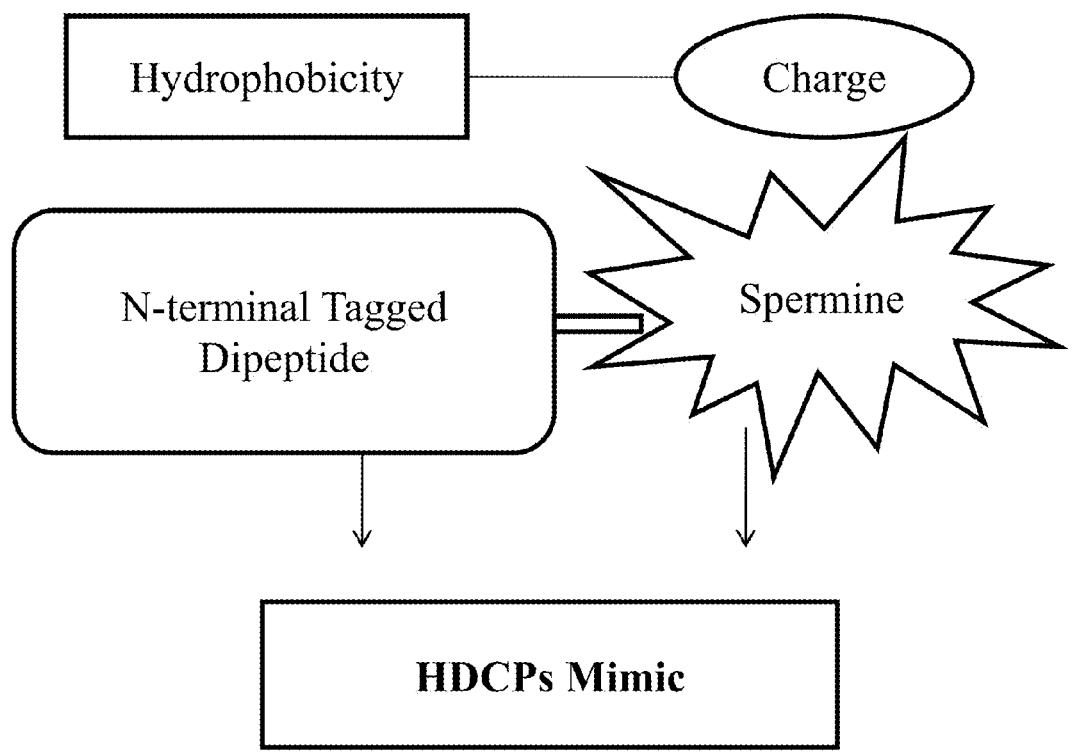
FIG. 1: Illustrates the design of polyamine conjugated peptidomimetics

Based on the pharmacophore of short antimicrobial peptidomimetics, various structure-activity relationships have been reported, where modifications in charge distribution or hydrophobicity have led to optimization of molecules for therapeutic applications [*J. Med. Chem.* 46:1567-1570, 2003; *Biopolymers*, 90:83-93, 2008]. In the present invention we report two series of peptidomimetics (Structure 1 and Structure 2) with linear/branched arrangements of Tryptophan (Trp) residues on the polyamine (spermidine/spermine) backbone to explore the effects on antibacterial activity and selectivity.

The general structure of template in present invention is represented by the following schematics:

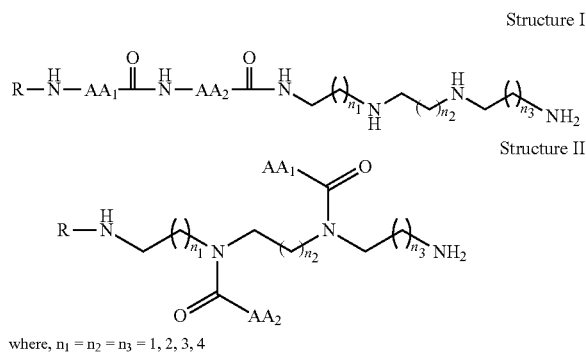

where, $n_1 = n_2 = n_3 = 1, 2, 3, 4$ wherein R can be hydrogen or any carboxylic acid moiety conjugated through amide bond (—CONH—), or ester bond (—COOR—) or 2-(4-(trifluoromethyl)phenyl) acetic acid, 2-(4-fluorophenyl)aceticacid, 4-(aminomethyl)benzoic acid, 4-(aminomethyl)benzoic acid, 3-(4-hydroxyphenyl)propanoic acid, 3-(3,4-dihydroxyphenyl)propanoic acid, 3-(3,4-dihydroxyphenyl)acrylic acid (Caffeic acid), (E)-3-(4-hydroxyphenyl)acrylic acid, (p-Hydroxycinnamic acid), cinnamic acid, [1,1'-biphenyl]-4-carboxylic acid, [1,1':4',1''-terphenyl]-4-carboxylic acid, [1,1':4',1''-terphenyl]-2-carboxylic acid, 2-naphthoic acid, 2-(naphthalen-2-yl)acetic acid, 9-fluorenyl methoxy carboxylic acid.

In still another embodiment of the present invention a peptidomimetic derivatives according to the structure I and II wherein R can be an aliphatic acid moiety conjugated with amide bond (—CONH—), at the C-terminal is specified as

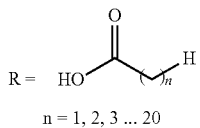

n = 1, 2, 3 ... 20

Further R can be unsaturated fatty acid such as oleic acid, linoleic acid or linolenic acid.

In certain embodiment in the structures claimed above the AA1 and AA2 are amino acids, wherein the amino acids can be tryptophan (W), Ornithine (O) lysine (K) or phenylalanine (F) or combinations of two amino acids. The sequence of dipeptide can be —WW—, —WO—, —WK—, —WF—, —OW—, —OO—, —OK—, —OF—, —FF—, —FW—, —FK—, —FO—.

The peptidomimetics designed in present invention were evaluated as antibacterial therapeutics against a broad range of bacterial strains by broth microdilution method. The antibacterial activity of the peptidomimetics was reported in terms of the minimum inhibitory concentrations (MIC). The term "MIC" refers to the lowest drug concentration that completely inhibits bacterial growth after 18-24 h incubation at 37° C.

Herein by "bacteria" we refer to both Gram-positive and Gram-negative bacteria. Examples of Gram negative bacterial species may be as follows: *Acinetobacter, Bordetella, Citrobacter, Escherichia, Fusobacterium, Haemophilus, Klebsiella, Proteus, Yersinia* and *Pseudomonas* species. Examples of Gram positive bacterial species include *Streptococcus, Staphylococcus, Actinomyces* and *Clostridium*.

In one feature of the invention, the peptidomimetics showing antibacterial activity were found to exert cell selective interactions as they are lytic particularly to the bacterial cell and non-toxic to the mammalian cells. The toxicity of peptidomimetics was screened by hemolytic activity against human RBCs and Lactate dehydrogenase [LDH] release assay on the peripheral blood mononuclear cells.

The present invention further provides the mode of action of designed active peptidomimetics against methicillin resistant *S. aureus*. Among the peptidomimetics the most active peptidomimetics showed rapid bactericidal kinetics, membrane depolarization and membrane disruptive mode of actions against MRSA. The mode of action was corroborated by the various biophysical and microscopic tools and techniques. The details of the mode of action studies have been given in the following examples.

MRSA is an extraordinary pathogen associated high mortality rates in clinical settings due to its virulence, multidrug-resistant profile, and prevalence in community and nosocomial environments. In yet another embodiment of the present invention it was found that the active molecules were effective to eradicate the bacterial cells embedded in MRSA biofilms. The term 'biofilm' here means microbial populations adhered to polystyrene surface (for different duration of time, young biofilms 6 h and mature biofilms 24 h) and producing slime due to accumulation of extracellular polymeric substance (EPS). The EPS matrix generally is composed of biopolymers including polysaccharides, proteins, nucleic acids and lipids.

In another embodiment of the invention these peptidomimetics inhibited the biofilms formation/eradicated pre-formed biofilm of MRSA formed on the biotic/abiotic surface. For determination of biofilm formation/killing abilities, we used a combination of the alamar blue assay (for measurement of viability) and crystal violet assay (for quantification of biomass).

It should be noted that in all the mentioned embodiments the present invention provides a novel and potent class of membrane-active antibacterial peptidomimetics against multidrug resistant infections that are also able to eradicate clinically relevant 24 h mature MRSA biofilms. Further evaluation of prevention of biofilm formation on solid supports like medical devices would broaden therapeutic applications of these peptidomimetics in clinical settings.

In another embodiment, a process for the preparation of peptidomimetics (1a-1f) of the present invention comprising the steps of:

pre-swelling the resin in DMF:DCM for a period ranging between 2 h to 4 h at a temperature in the range of 25 to 30° C. followed by adding spermine in a solvent to obtain pre-swelled resin;

capping the pre-swelled resin obtained in step (a) by using the solvent (capping agent) for a period of time 30 min followed by protecting the terminal primary amino group of spermine with Dde-OH in DMF for a period of time ranging between 6 h to 12 h followed by protecting secondary amino group by using the Boc-anhydride in the presence of catalyst for a period of time ranging between 2 h to 4 h to obtain protected resin;

removing the Dde protection of terminal primary amino group from the protected resin obtained in step (b) by using 2% solution of hydrazine in a solvent followed by coupling of N-terminal amino group with Fmoc-Trp(Boc)-OH in the presence of HOBt and DIPCDI followed by removal of Fmoc group by 20% piperidine. Again the N-terminal was coupled with second Fmoc-Trp(Boc)-OH in the presence of HOBt and DIPCDI followed by removal of Fmoc group by 20% piperidine to get dipeptide and finally N-terminal amino group was tagged by R group using HOBt and DIPCDI in DCM:DMF to obtain peptidomimetics (1a-1f);

finally deprotecting the peptidomimetics from resin obtained in step (c) by using (DCM:TFA:ethanedithiol:triisopropylsilane:phenol:water: in ratio 65:30:2:1:1:1) followed by precipitation and washing to get peptidomimetics (1a-1f)

In another embodiment, a process for the preparation of peptidomimetics (2a-2f) of the present invention comprising the steps of:

pre-swelling the resin in DMF:DCM for a period ranging between 2 h to 4 h at a temperature in the range of 25 to 30° C. followed by adding spermine in a solvent to obtain pre-swelled resin;

capping the pre-swelled resin obtained in step (a) by using the solvent (capping agent) for a period of time 30 min followed by protecting the terminal primary amino group of spermine with Dde-OH in a solvent for a period of time ranging between 6 h to 12 h followed by coupling with Boc-Trp(Boc)-OH, HOBt, DIPCDI in a mixture of solvent to get the protected resin;

removing the Dde-OH protection of terminal primary amino group from the protected resin obtained in step (b) by using 2% solution of hydrazine in a solvent followed by coupling with N-terminal tagging (R group) in the presence of HOBt and DIPCDI in a mixture of solvent DCM:DMF to obtain peptidomimetics (2a-2f);

finally deprotecting the peptidomimetics from resin obtained in step (c) by using (DCM:TFA:ethanedithiol:

triisopropylsilane:phenol:water: in ratio 65:30:2:1:1:1) followed by precipitation and washing to get peptidomimetics (2a-2f).

In another embodiment of the invention, these peptidomimetics are formulated along with pharmaceutically acceptable drug delivery vehicle to obtain a composition. The said composition comprises any of the peptidomimetics in the form of emulsions, liquids, cream, ointment or paste alone or in combination. Further, the composition comprising any of the peptidomimetics of the present invention may be useful for treatment of skin infections, systemic infections, burns or wounds healing in humans or animals.

EXAMPLES

The following examples are given by way of illustration of the present invention and therefore should not be construed to limit the scope of the present invention.

Example 1

Fmoc-protected amino acids and resins were purchased from Novabiochem (Darmstadt, Germany), N, N-Diisopropylcarbodiimide (DIPCDI, cat. no. D12, 540-7), 1-hydroxybenzotrizole (HOBt, cat. no. 54804), Di-isopropylethylamine (DIPEA, cat. no. D-3887), N-methylpyrrolidinone (NMP, cat. no. 494496), piperidine (cat. no. 411027), spermine (cat. no. S3256), triisopropylsilane (TIS, cat. no. 23378-1), crystal violet (cat. no. C3886), glucose (cat. no. G7528), hydrazine (cat. no. 225819), 3,3'-dipropylthiadicarbocyanine iodide (DiSC35, cat. no. 43608) and TOX-7 kit (LDH release assay kit) were obtained from Sigma-Aldrich. Trifluoroacetic acid (TFA, cat. no. 80826005001730) and 2-Acetyldimedone (Dde-OH, cat. no. 8.51015.0005) were purchased from Merck company. All the moieties used as N-terminal tag were purchased from Sigma-Aldrich. Tryptone Soya broth (TSB, cat. no. M011-500G) was purchased from HIMEDIA, India and Mueller Hinton broth (MHB) and agar were purchased from DIFCO (Franklin Lakes, N.J., USA). Alamar blue reagent (cat. no. DAL 1025) and LIVE/DEAD BacLight (L7012) assay kit were procured from Invitrogen (Molecular Probes, Eugene, Oreg., USA). HPLC grade and solvents were obtained from Merck (Germany). Dimethylformamide (DMF) and dichloromethane (DCM) were obtained from Merck (Mumbai, India). DMF was double distilled prior to use.

Example 2

Synthesis and Characterization of Peptidomimetics

The peptidomimetics were synthesized by solid phase peptide synthesis on 2-chlorotrityl chloride resin using Fmoc strategy as described previously with minor modifications [*Tetrahedron Lett.* 41, 1095-1098, 2000]. Briefly, the resin was pre-swelled in DMF:DCM (1:1, v/v) for 2 h and then 5 eq. of spermine (in DCM) was added. The reaction was run for 4 h under inert atmosphere. Completion of reaction was monitored through Kaiser Test [*Anal. Biochem.*, 34: 595-598, 1970]. After coupling, the resin was capped with methanol for 30 min. The terminal primary amino group of spermine was protected with 2 eq. of Dde-OH in DMF overnight. After protection of primary amino group, secondary amino groups were protected with 6 eq. of Boc-anhydride in presence of DIPEA for 4 h. Then Dde-OH protection of primary amines was removed using 2% w/v hydrazine (in DMF). Further two couplings were done with Fmoc-Trp (Boc)-OH in presence of HOBt and DIPCDI in DCM:DMF (1:1). The N-terminal tagging was done with 4 eq. of unnatural tag, HOBt and DIPCDI in DCM:DMF (1:1) leading to peptidomimetics 1a-1f (Scheme 1).

Scheme 1

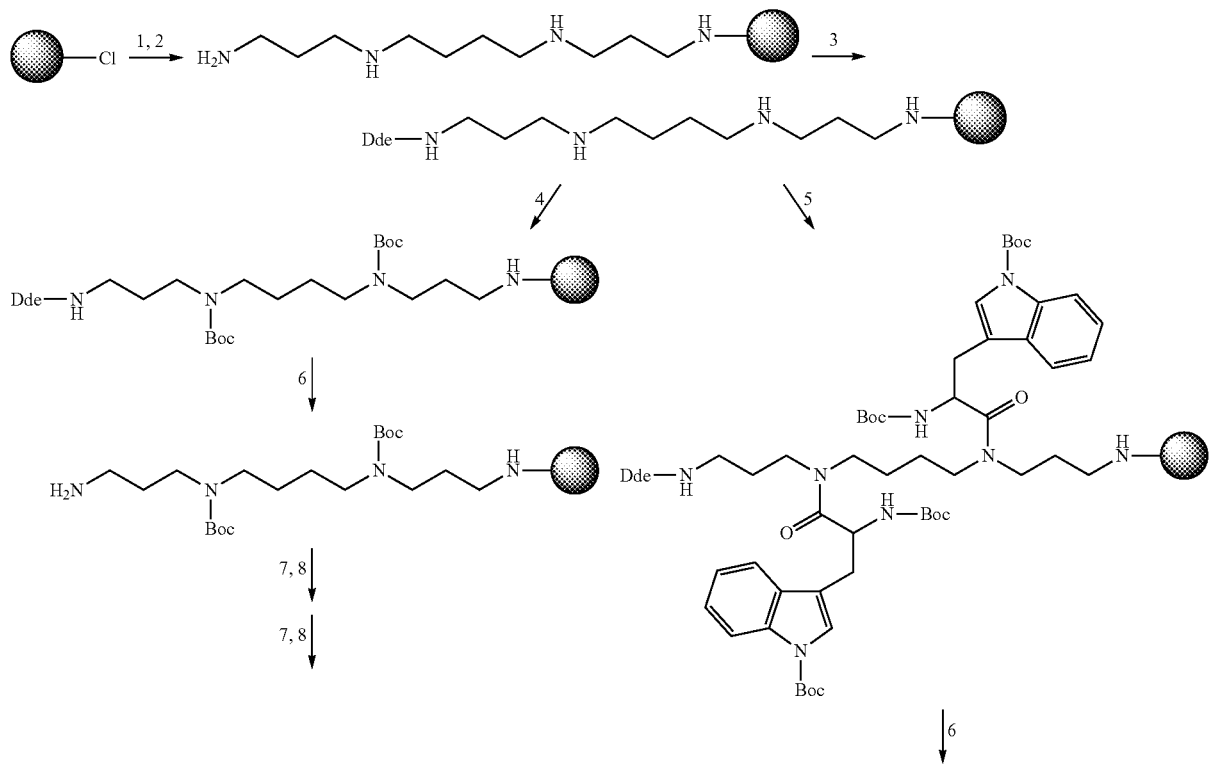

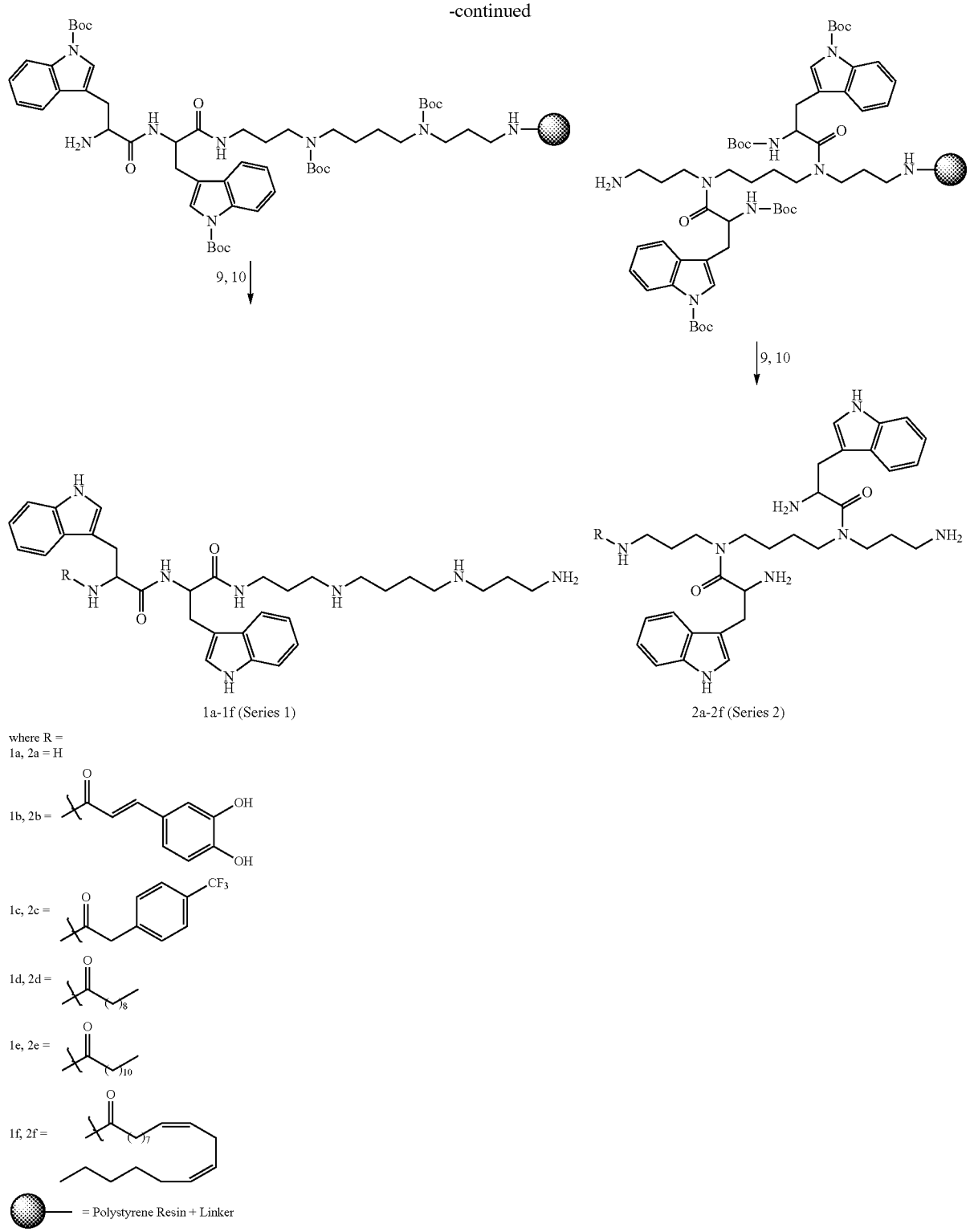

1a-1f (Series 1)  2a-2f (Series 2)

where R =
1a, 2a = H

Reagents and Conditions:

1) 5 eq. Spermine, DCM, 3 h, 2) MeOH for 30 min. 3) 2 eq. Dde-OH, DMF, overnight 4) 6 eq. (Boc)$_2$O, DCM:DMF (1:1), 3 h, 5) Boc-Trp(Boc)-OH, HOBt, DIPCDI, DCM:DMF (1:1), overnight, 6) 2% hydrazine (DMF), 7) Fmoc-Trp(Boc)-COOH, HOBt, DIPCDI, DCM:DMF (1:1), 1.5 h, 8) 20% piperidine (DMF), 9) 3 eq. R—COOH, HOBt, DIPCDI, DCM:DMF (1:1), overnight, 10) 30% TFA/DCM.

For syntheses of peptidomimetics 2a-2f, Dde-OH protected resin was coupled with 4 eq. of Boc-Trp (Boc)-OH, HOBt and DIPCDI. Thereafter, deprotection of primary amine group was done with 2% w/v hydrazine in DMF. The N-terminal tagging was achieved as described above. Final deprotection of peptidomimetics from resin in both series was performed using a cleavage cocktail (DCM:TFA:ethanedithiol:triisopropylsilane:phenol:water: in ratio 65:30:2:1:1:1). The cleavage cocktail was filtered and to the filtrate cold diethyl ether was added to effectuate peptide precipitation. After washing the crude peptide twice, the solid was dissolved in methanol and desalted using LH-20 sephadex (Sigma) column. Further the peptidomimetics were purified on RP-HPLC, using a semi-preparative column (7.8×300 mm, 125 Å, 10-μm particle size) with gradient of 10 to 90% buffer 2, where, buffer 1 was water (0.1% TFA) and buffer 2 was acetonitrile (0.1% TFA) over 45 min. The peptidomimetics after purification were confirmed either by LC-MS/MS (Quattro micro API, Waters) or UHPLC (Dionex, Germany) and LTQ Orbitrap XL (Thermo Fisher Scientific, USA) mass determination. All the designed peptidomimetics were >80% pure and their masses were in the range of 575-850 Da (Table 1).

TABLE 1

Peptidomimetics, % purity, % acetonitrile at RP-HPLC elution and molecular mass of designed peptidomimetics

| Peptidomimetics | Purity | % of acetonitrile[a] | Mass [M + H]⁺ Calc. | Mass [M + H]⁺ Obs. |
|---|---|---|---|---|
| 1a | 95 | 17.41 | 575.3816 | 575.3808 |
| 1b | 99 | 46.42 | 737.4133 | 737.4139 |
| 1c | 95 | 54.72 | 761.4109 | 761.4110 |
| 1d | 95 | 61.57 | 729.5174 | 729.5178 |
| 1e | 95 | 65.21 | 757.5487 | 757.5489 |
| 1f | 98 | 70.36 | 837.6113 | 837.6097 |
| 2a | 80 | 12.30 | 575.3816 | 575.3815 |
| 2b | 80 | 44.34 | 737.4133 | 737.4140 |
| 2c | 83 | 49.85 | 761.4109 | 761.4118 |
| 2d | 99 | 57.92 | 729.5174 | 729.5181 |
| 2e | 99 | 62.63 | 757.5487 | 757.5495 |
| 2f | 99 | 69.78 | 837.6113 | 837.6113 |

[a]Percentage of acetonitrile at RP-HPCL elution of peptidomimetics

Example 3

Antibacterial Activity

Following bacterial strains were used in this study: S. aureus (ATCC 29213), methicillin resistant S. aureus (ATCC 33591), Staphylococcus epidermidis (ATCC 12228), methicillin resistant Staphylococcus epidermidis (ATCC 51625), Enterococcus faecalis (ATCC 7080), Escherichia coli (ATCC 11775), and Acinetobacter baumannii (ATCC 19606). Antibacterial activity was evaluated using a modified serial broth dilution method in accordance with Clinical Laboratory Standard Institute guidelines [Methods for dilution antimicrobial susceptibility tests for bacteria that grow aerobically-7th ed. Approved standard M7-A7. Clinical and Laboratory Standards Institute, Wayne, Pa., Biochim. Biophys. Acta 1798:1864-1875, 2010.]. Briefly, the inoculums were prepared from mid-log phase bacterial cultures. Peptidomimetics were incubated with bacterial suspension in Muller Hinton broth media (10⁵ CFU/mL) in 96 well microtitre plate. The plates were incubated overnight with agitation (200 rpm) at 37° C. After 18 h, absorbance was measured at 630 nm. Cultures without test peptidomimetics were used as positive control. Un-inoculated Mueller Hinton Broth (MHB) was used as negative control. Tests were carried out in duplicate on at least three different days. Minimum inhibitory concentration (MIC) is defined as the lowest concentration of peptidomimetics that completely inhibited growth. For comparison standard peptide antibiotics vancomycin (VAN) and polymyxin B (PMB) were also assayed under identical conditions (Table 2). Template peptidomimetics 1a showed moderate activity against Gram-positive bacterial strains while peptidomimetics 1b-1f displayed good activity with MIC <10 μg/mL against all the tested strains except E. faecalis. Against Gram-negative bacteria E. coli also peptidomimetics in series 1 showed activity with MIC in the range of 14.2-56.8 μg/mL. In series 2 peptidomimetics 2a and 2b showed poor activity, while peptidomimetic 2c showed moderate activity, but, 2d-2f exhibited good growth inhibition of all the bacterial stains tested (MIC: 0.8-28.4 μg/mL) except A. baumannii. Standard antibiotic PMB showed relatively poor activity against Staphylococcus species, although it showed excellent growth inhibition of Gram-negative bacterial strains. VAN showed potent growth inhibition for Staphylococcus species, however, was ineffective against Gram-negative strains under the experimental conditions. Further, antibacterial activity of active peptidomimetics 1c and 1d were also evaluated against MRSA in presence of 25% v/v human serum as well as bovine serum. A 4 fold and 8 fold increase in MIC was observed for 1c and 1d, respectively, in human serum.

TABLE 2

Antibacterial activity of peptidomimetics against Gram-positive and Gram-negative bacterial strains and cytotoxicity against blood cells

| | MIC(μg/L) | | | | | | | | |
|---|---|---|---|---|---|---|---|---|---|
| | S. aureus (ATCC 29213) | MRSA (ATCC 33591) | S. epidermidis (ATCC 12228) | MRSE (ATCC 51625) | E. facaelis (ATCC 7080) | E. coli. (ATCC 11775) | A. baumannii (ATCC 19606) | % H[a] (250 μg/mL) | % LDH[b] release (20 μg/mL) |
| 1a | 113.6 | 227.2 | 113.6 | ND | 454.5 | ND | ND | 4 | ND |
| 1b | 3.5 | 7.1 | 3.5 | 7.1 | 113.6 | 14.2 | ND | 16 | ND |
| 1c | 1.7 | 3.5 | 1.7 | 3.5 | 28.4 | 56.8 | 28.4 | 2 | 5.78 |
| 1d | 1.7 | 1.7 | 1.7 | 1.7 | 3.5 | 14.2 | 113.6 | 9 | 17.5 |
| 1e | 1.7 | 3.5 | 1.7 | 1.7 | 7.1 | 14.2 | 56.8 | 31 | ND |
| 1f | 7.1 | 3.5 | 1.7 | 7.1 | 28.4 | 28.4 | ND | 30 | ND |
| 2a | >454.4 | >227.2 | >454.4 | 227.2 | ND | >454.4 | ND | 0 | ND |
| 2b | >454.4 | 454.4 | ND | ND | ND | >454.4 | ND | 5 | ND |
| 2c | 14.2 | 28.4 | 7.1 | 14.2 | ND | 113.6 | 113.6 | 1 | ND |
| 2d | 0.8 | 1.7 | 0.8 | 1.7 | 28.4 | 28.4 | 113.6 | 83 | ND |
| 2e | 0.8 | 1.7 | 0.8 | 1.7 | 7.1 | 28.4 | 113.6 | 96 | ND |

TABLE 2-continued

Antibacterial activity of peptidomimetics against Gram-positive and
Gram-negative bacterial strains and cytotoxicity against blood cells

| | MIC(μg/L) | | | | | | | | |
|---|---|---|---|---|---|---|---|---|---|
| | S. aureus (ATCC 29213) | MRSA (ATCC 33591) | S. epidermidis (ATCC 12228) | MRSE (ATCC 51625) | E. facaelis (ATCC 7080) | E. coli. (ATCC 11775) | A. baumannii (ATCC 19606) | % H[a] (250 μg/mL) | % LDH[b] release (20 μg/mL) |
| 2f | 0.8 | 3.5 | 0.8 | 1.7 | 14.2 | 28.4 | 56.8 | 88 | ND |
| PMB | 14.2 | 28.4 | 7.1 | 28.4 | 113.6 | 0.4 | ND | ND | ND |
| VAN | 0.4 | 0.8 | 0.4 | 0.8 | ND | 113.6 | 56.8 | ND | ND |

[a]Percentage hemolysis of human RBCs,
[b]% LDH release against peripheral blood mononuclear cells

Example 4

Hemolytic Activity

Hemolytic activity of the peptidomimetics was evaluated on human red blood cells (hRBC) as described previously with minor modifications [FEBS J, 273:4040-4054, 2006; Biochim Biophys Acta., 1798:1864-1875, 2010]. Briefly, 100 μL of fresh hRBC suspension 4% v/v in NaCl/Pi (35 mM phosphate buffer, 150 mM NaCl, pH 7.2) was placed in a 96-well plate. After incubation of the peptidomimetics (100 μL) in the hRBC suspension for 1 h at 37° C., the plates were centrifuged and supernatant (100 μL) was transferred to fresh 96-well plate. Absorbance was read at 540 nm using ELISA plate reader (Molecular Devices). Percent hemolysis was calculated using the following formula:

% hemolysis=$100[(A-A_0)/(A_t-A_0)]$

Where, A represents absorbance of sample wells at 540 nm. Also $A_0$ and $A_t$ represents 0% and 100% hemolysis determined in NaCl/Pi and 1% Triton X-100, respectively (Table 2). Most of the peptidomimetics including 1a-1d, and 2a-2c were found to cause minimal hemolysis up to the maximum concentration tested. Peptidomimetics 1e and 1f caused 31% and 30% hemolysis at 250 μg/mL. Peptidomimetics 2d, 2e and 2f caused significant hemolysis with 83%, 96% and 88% damage to hRBCs at 250 m/mL respectively.

Example 5

Cytotoxicity Assay in Peripheral Blood Mononuclear Cells (PBMCs)

For the experiment a protocol as used previously was employed with minor modifications [J. Immunol. Methods, 115:61-69, 1988; Chem. Biol. 20:1286-1295, 2013.]. Briefly, blood was collected from healthy human donors in sodium heparin anticoagulant tubes in accordance with institutional guidelines. The blood was diluted 1:1 with NaCl/Pi (35 mM phosphate buffer, 150 mM NaCl, pH 7.2). Blood cells were separated over histopaque (Sigma-aldrich) by centrifugation for 30 min at 1200 rpm. The PBMCs were collected and washed twice with NaCl/Pi (35 mM phosphate buffer, 150 mM NaCl, pH 7.2). The cells were then re-suspended in complete RPMI 1640 medium (Himedia) supplemented with 10% FBS (Sigma) and quantified by trypan blue exclusion on microscope. PBMCs ($1\times10^6$ cells/mL) in complete media were seeded into a 24-well plate and left in the incubator for 2 h at 37° C. in 5% CO2. The cells were then treated with 1c, 1d and VAN at desired concentrations (20 μg/mL). 2% Triton X-100 was used as a negative control. After 24 h of incubation, the content of each well was transferred to sterile 1.5 mL eppendorf tube and cells were pelleted at 2000 rpm for 10 min. The supernatant was assessed for the release of LDH by using the TOX7 kit (Sigma). The experiments were carried out in duplicate on three different days and data is presented as mean±S.D. At 20 μg/mL concentrations 5.78±6.58% and 17.56±10.15% LDH release was caused by 1c and 1d, respectively (Table 2).

Example 6

Membrane Depolarization Mode of Action

Figure 2:
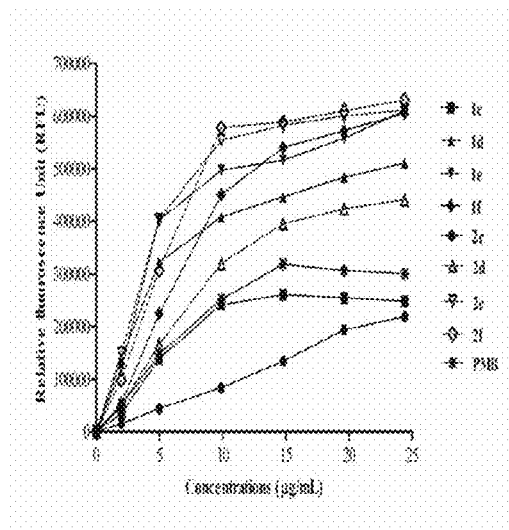
FIG. 2: Illustrates the concentration dependent cell membrane depolarization assessed by potential sensitive dye $DiSC_3(5)$ in intact *S. aureus* cells.

For determination of membrane depolarizing ability of designed peptidomimetics, a membrane potential sensitive dye $DiSC_3(5)$ was used as described previously with minor modifications [Org Biomol. Chem. 10: 8326-8335, 2012; J. Am. Chem. Soc., 132: 18417-18428, 2010.]. Briefly, overnight grown MRSA was sub cultured into MHB for 2-3 h at 37° C. to obtain mid-log phase cultures. The cells were centrifuged at 4000 rpm for 10 min at 25° C., washed, and re-suspended into respiration buffer (5 mM HEPES, 20 mM glucose, pH 7.4) to obtain a diluted suspension of $OD_{600}$~0.05. Then $DiSC_3(5)$ [0.18 μM in DMSO], was added to 500 μL aliquotes of the re-suspended cells and allowed to stabilize for 1 h. Baseline fluorescence was acquired using a Edinburg F900 spectrofluorometer by excitation at 622 nm and emission at 670 nm in a 1 cm path length cuvette. Bandwidth of 5 nm was employed for excitation and emission. Subsequently, increasing concentrations of test peptidomimetics were added to the stabilized cells and the increase of fluorescence on account of the de-quenching of $DiSC_3(5)$ dye was measured after every 2 min to obtain the maximal depolarization. Increase in relative fluorescence unit (RFU) was plotted against increasing concentrations of different peptidomimetics or PMB. For peptidomimetics 1a and 2a, only minor increase in relative fluorescence unit (RFU) were observed up to the maximum concentration tested, suggesting inability of these peptidomimetics to alter membrane potential at concentrations below MIC (data not shown). For peptidomimetics 1c and 2c with aromatic N-terminal tags, only marginal changes in RFU were observed up to the highest concentration tested (FIG. 2). For peptidomimetics 1d and 2d, intermediate changes in fluorescence intensity were observed, whereas for peptidomimetics 1e, 1f, 2e and 2f, significant changes in RFU were observed. The increase in fluorescence for lipid tagged peptidomimetics was concentration dependent up to 9.9 μg/mL and henceforth, got saturated resulting into plateau like dose response curves. The experiment was repeated twice on two consecutive days and produced similar results.

Example 7

Killing Kinetic Study

Figure 3:
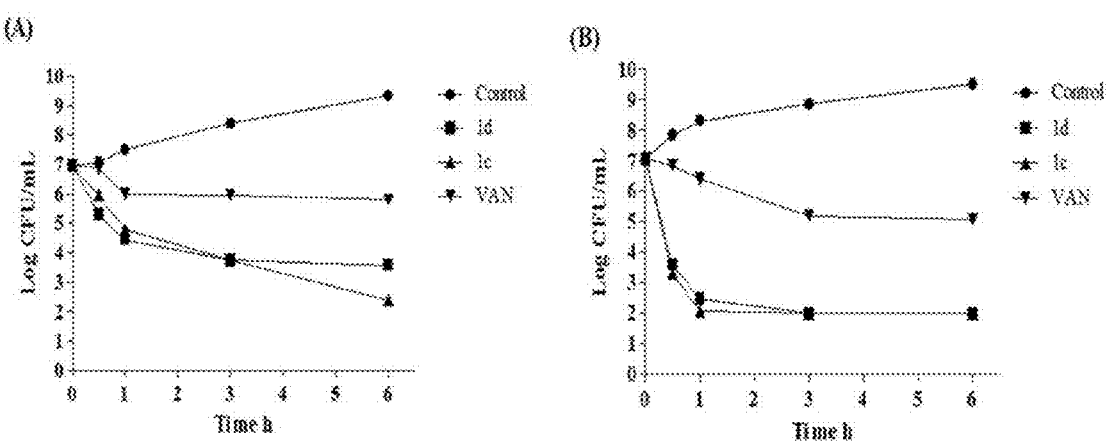
FIG. 3: Illustrates bactericidal kinetic of designed peptidomimetics incubated with *S. aureus* ATCC 33591, where (A) Killing curve at 2×MIC and (B) Killing curve with 4×MIC of compounds 1c, 1d and Vancomycin (VAN) and sampled at the indicated time points.

The killing kinetics of MRSA (ATCC 33591) by peptidomimetics was evaluated as described previously with minor modifications [*Antimicrob. Agents Chemother.*, 18: 699-708, 1980.]. Briefly, log-phase bacteria (1.2-3.0×10$^7$ CFU/mL) were incubated with peptidomimetics 1c, 1d and VAN at 2× and 4× their respective MIC in MHB. Aliquots were removed after fixed time interval (0.5, 1, 2, 3, and 6 h) and diluted appropriately in sterile saline before plating on the Mueller Hinton II agar. The plates were incubated for at 37° C. for 24 h and CFU were counted. At 2×MIC, both peptidomimetics reduced ≥3-log$_{10}$ CFU/mL within 3 h of incubation whereas at 4×MIC, bactericidal effect was observed within 30 min of incubation by reduction of >4-log$_{10}$ CFU/mL (FIG. 3).

Example 8

Scanning Electron Microscopy (SEM)

Figure 4:
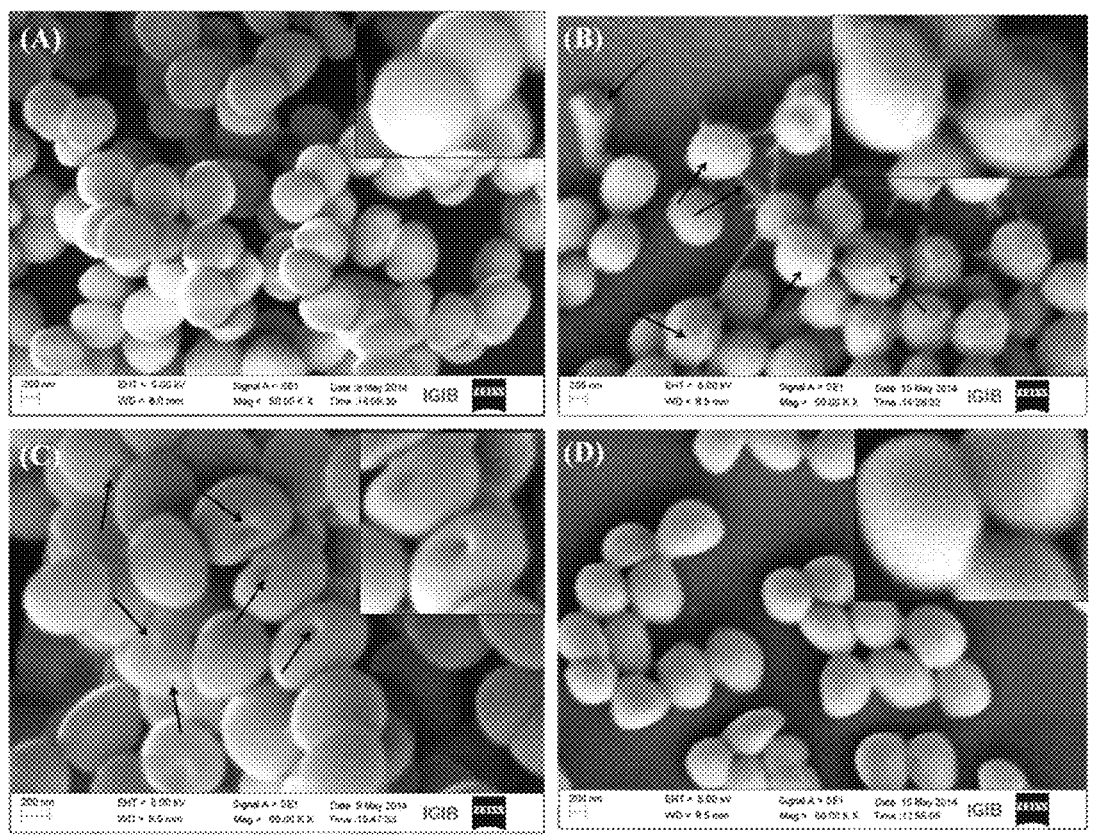
FIG. 4: Illustrates scanning electron microscopic images of MRSA. (A) Untreated bacterial cells, (B) cells treated with compound 1c, (C) cells treated with compound 1d and (D) cells treated with VAN. The cells were exposed to various agents for 30 min at 10× their respective planktonic MIC. The arrows point at morphological alterations caused. Higher magnification (150KX) images of each image have been given in inset.

To visualize the effect of peptidomimetics on MRSA cells we carried out electron microscopic investigation using a protocol described previously with slight modifications [*Antimicrob. Agents Chemother.*, 55:1920-1929, 2011; *Antimicrob Agents Chemother.*, 58:5435-5447, 2014.]. For this, freshly inoculated MRSA (ATCC 33591) was grown on MHB up to OD600~0.5 (corresponding to 10$^8$ CFU/mL). Bacterial cells were then spun down at 4000 rpm for 15 min, washed thrice with NaCl/Pi (10 mM phosphate buffer, 150 mM NaCl, pH 7.4) and re-suspended in equal volume of NaCl/Pi. For SEM experiment, a higher bacterial inoculums (10$^8$ CFU/mL) was used therefore the cells were incubated with test peptidomimetics 1c, 1d or VAN at respective 10×MIC for 30 min. Controls were run in the absence of antibacterial agents. After 30 min, the cells were spun down and washed with NaCl/Pi thrice. For cell fixation, the washed bacterial pallet was re-suspended in 0.5 mL of 2.5% paraformaldehyde in NaCl/Pi and was incubated at 4° C. for overnight. After fixation, cells were spun down and washed with 0.1M sodium cacodylate buffer twice and fixed in 1% osmium tetraoxide in 0.1M sodium cacodylate buffer at RT for 40 min in dark. Further the samples were dehydrated in series of graded ethanol solutions (30% to 100%), and finally dried in desiccators under reduced pressure. Upon dehydration, the cells were air dried for 15 min in dark at RT after immersion in hexamethyldisilazane. An automatic sputter coater (Quorum-SC7640) was used for coating the specimens with thickness of 30 A° gold particles. Then samples were imaged via scanning electron microscope (Zeiss EVO LS15). Control MRSA cells exhibited bright smooth appearance with intact cell membrane (FIG. 4A). Peptidomimetic 1c treatment caused rough and damaged surfaces, cell bursting, leakage and string-like substances, which are considered to be cellular debris arising from cell lysis (FIG. 4B). For peptidomimetic 1d treated cells appeared distorted with depression and hole formation (FIG. 4C), indicating the membrane active mode of action for designed peptidomimetics. Surprisingly, VAN treated cells mostly retained their smooth appearance, albeit slight deformations in shape of cells as compared to control cells (FIG. 4D).

Example 9

Resistance Development Study

Figure 5:
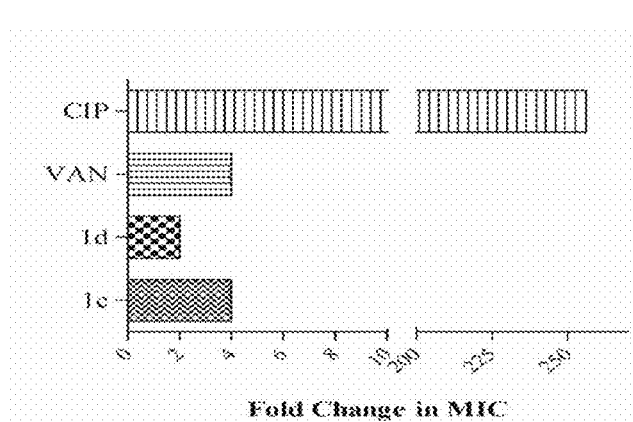
FIG. 5: Illustration of resistance development study in *S. aureus* (ATCC 33591) after 17 serial passages with sub MIC of 1c/1d or antibiotic treatment. The fold change in MIC is the ratio of the MIC after 17 passages relative to that MIC observed before first passage.

To determine potential of active peptidomimetics against resistance development, in vitro serial passage method at sub inhibitory concentration was done. Briefly, bacterial suspension (100 μL) from duplicate wells at the concentration of sub-MIC was used to inoculate fresh culture. The culture was grown to obtain approximately 10$^5$ CFU/mL for the next experiment. These bacterial suspensions were then incubated with desired concentration of antibacterial agents for 18 h to determine new MIC. The same sub culturing protocol was used for next 16 passages and MIC was determined using OD$_{630\ nm}$ as described previously in the text [*Chem. Biol.*, 20:1286-1295, 2013.] A 4 fold and 2 fold increase in MIC was observed for 1c and 1d respectively (FIG. 5). For standard antibiotics VAN after 17 passages, the MIC was increased by 4 fold, whereas for ciprofloxacin (CIP), a radical change of 256 fold in MIC was observed.

Example 10

Biofilm Susceptibility Assay

To evaluate potential of designed active peptidomimetics against MRSA biofilms a methodology as used previously was employed with minor modifications [*Antimicrob. Agents Chemother.*, 57:2726-2737, 2013]. Briefly, freshly inoculated MRSA (ATCC 33591) was grown in biofilm growth media (TSB supplemented with 0.5% w/v NaCl and 0.25% w/v glucose) overnight. Next day, the culture was diluted in fresh biofilm growth media to 10$^5$ CFU/mL. 200 μl of diluted culture was dispensed in wells of a 96-well polystyrene plate for biofilm formation. To evaluate the inhibition of biofilm formation, antibacterial agents at MIC$_b$ (planktonic MIC in biofilm media) and sub-MIC$_b$ concentrations were added initially with diluted culture following incubation at 37° C. without shaking Another set of experiment was performed by addition of fresh medium containing antibacterial agents at 10×MIC$_b$ and 20×MIC$_b$ concentrations after gently washing by sterile NaCl/Pi buffer (35 mM phosphate buffer, 150 mM NaCl, pH 7.4) to 24 h preformed biofilm. Biofilm cultures were re-incubated at 37° C. for 24 h. After removal of medium, the biofilms were further washed twice with sterile NaCl/Pi buffer and assessed for metabolic activity (alamar blue assay) and biomass quantification (Crystal violet assay).

For visualization of biofilm and validation of AB and CV assay we performed confocal microscopy. For this biofilm formation was induced on glass cover slips in a 6-well plate. The biofilm on cover slips were washed twice with sterile NaCl/Pi buffer and stained with a Live/Dead kit reagent (Invitrogen, Molecular Probes, Eugene, Oreg., USA) following the manufacturer's instructions. This stain contains DNA binding dyes SYTO 9 (green fluorescent) and propidium iodide (PI; red fluorescent). When used alone, SYTO 9 stains all bacteria in a population, those with intact as well as damaged membranes. In contrast, PI penetrates only bacteria with damaged membranes, causing a reduction in the SYTO 9 stain (green fluorescence). The biofilms were examined with an Olympus flow view FV1000 (confocal laser scanning microscope, CLSM). The experiment was repeated three times on three different days and representative data is presented here.

Figure 6:
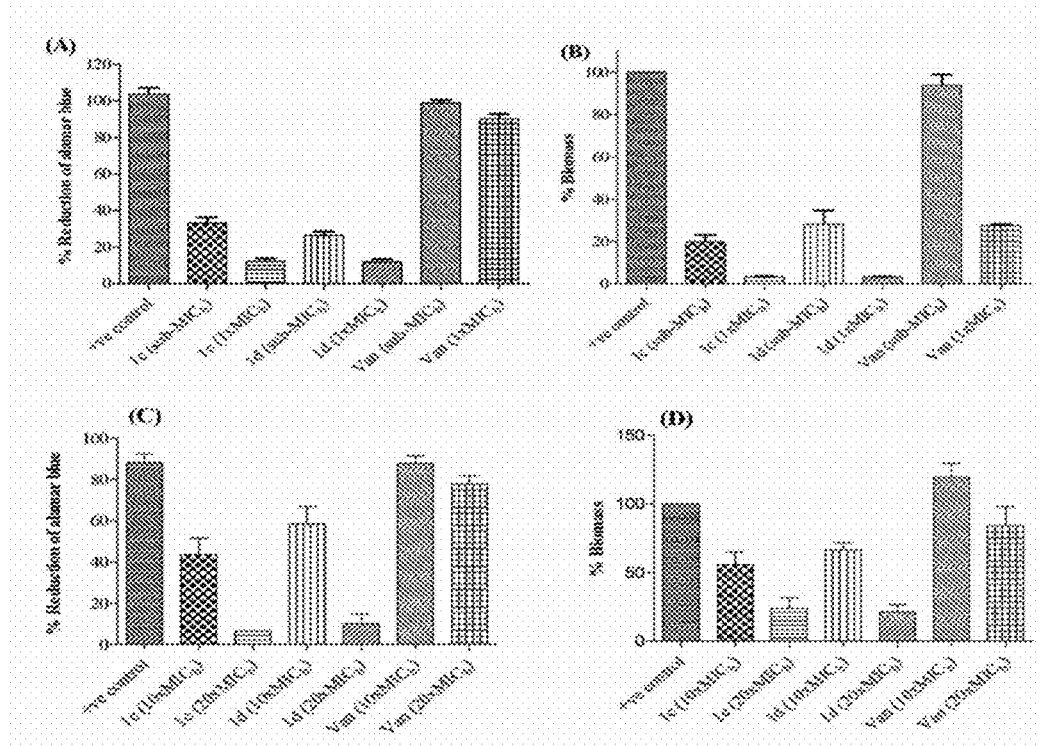
FIG. 6: Illustration (A, B) is Inhibition of MRSA biofilm formation by different agents using alamar blue assay and biomass quantification using crystal violet staining assay, respectively. In (C), (D) is metabolic activity of 24 h mature biofilm embedded MRSA using alamar blue assay and biomass quantification using crystal violet, respectively. Where, $MIC_b$ is planktonic MIC in biofilm media for 1c, 1d and VAN was 7.1 µg/mL, 3.5 µg/mL and 0.8 µg/mL, respectively. For all experiments data is expressed as mean±SD. Statistical differences from the control were determined by one-way analysis of variance (ANOVA) with Tukey's multiple comparison post hoc tests. All differences between the control and treated biofilms were considered statistically significant (*$P<0.001$).

Peptidomimetics 1c and 1d were able to halt biofilm formation at sub-MIC$_b$ concentrations as was evaluated using AB assay whereby a reduction in metabolic activity up to 33.1±5.7% and 26.4±3.3%, respectively was observed for 1c and 1d treated cells respectively. Similarly, % biomass reduction was found to be 19.8±5.6% and 28.2±11.1% for 1c and 1d respectively (FIGS. 6A and 6B). At $MIC_b$ concentration both peptidomimetics inhibited adhesion of biofilm causing >90% reduction in measured viability and biomass quantity. Further, against 24 h pre-formed mature biofilms at $20×MIC_b$ designed peptidomimetics 1c (140 μg/mL) and 1d (70 μg/mL) showed better killing profiles with 6.4±0.2 and 10.1±7.8% viable cells, respectively in comparison to 77.7±7.0% viable cells for VAN (20 μg/mL) at the indicated concentration (FIG. 6C). In parallel peptidomimetic 1c (at 140 μg/mL concentrations) and 1d (at 70 μg/mL concentrations) reduced biomass to 24.0±13.4% and 21.4±9.2% respectively as compared to control biomass (FIG. 6D). For VAN even at $20×MIC_b$ (20 μg/mL) the biomass remaining was 83 0.7±24.1%.

Figure 7:
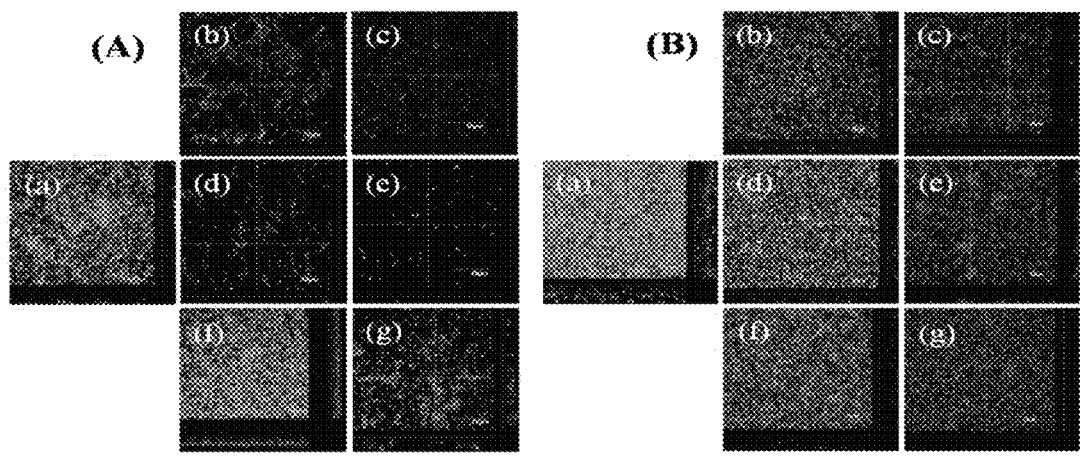
FIG. 7: Illustrates 3D images of MRSA biofilm, A) Effect of antibacterial agents on biofilm formation of MRSA using confocal laser scanning microscopy. In a) Control, b) 1c (sub-$MIC_b$), c) 1c ($MIC_b$), d) 1d (sub-$MIC_b$), e) 1d ($MIC_b$), f) VAN (sub-$MIC_b$), and g) VAN ($MIC_b$). B) Effect of antibacterial agents against 24 h mature preformed MRSA biofilm using confocal laser scanning microscopy. In a) control, b) 1c (10×$MIC_b$), c) 1c (20×$MIC_b$), d) 1d (10×$MIC_b$), e) 1d (20×$MIC_b$), f) VAN (10×$MIC_b$), and g) VAN (20×$MIC_b$). After treatment at different concentrations the biofilms were stained with Syto9 (green; viable cells) and propidium iodide (red; dead cells) as described by manufacturers' protocol.
Figure 8:
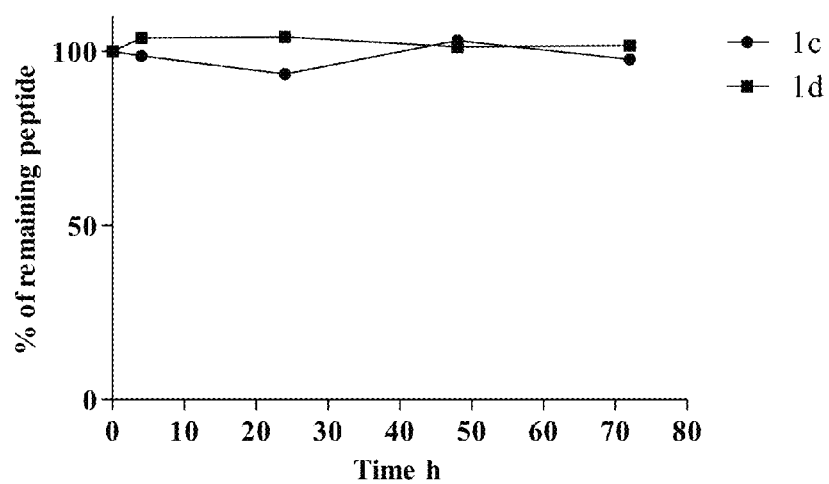
FIG. 8: Serum stability assay of peptidomimetics at 37° C. using RP-HPLC.

We next measured the thickness of biofilm using z-stacking in confocal microscopy. The control biofilm (24 h) showed a lawn of viable (green) cells with average thickness 14.3±1.4 μm (FIG. 7A). At $MIC_b$, 1c and 1d prevented formation of biofilm in which very few cells were adhered to substratum with observed average thickness of 3.9±1.1 μm and 3.5±0.6 μm, respectively. Furthermore, at sub-$MIC_b$ concentration the observed thicknesses were 5.2±0.3 μm and 5.8±0.4 μm (FIG. 7A.b and FIG. 7A.d). In case of VAN at $MIC_b$, the measured thickness of biofilm was 11.4±2.9 μm (FIG. 7A.g), whereas at sub-$MIC_b$ VAN was unable to reduce biofilm thickness.

Untreated 48 h mature biofilm (24+24) showed a lawn of viable (green) cells with average thickness of 23.6±2.5 μm (FIG. 7B). Subsequent to treatment with 1c and 1d at concentrations of $10×MIC_b$, in FIGS. 7B.b and 7B.d, there were visual decrease in the number of live cells and thickness was reduced to 7.1±1.5 and 7.0±1.0 μm, respectively. For peptidomimetics 1c and 1d, most of the cells lost their integrity at $20×MIC_b$, appearing red (FIG. 7B.c and FIG. 7B.e) and a smear of permeabilized cells was observed. Upon VAN treatment, no significant difference in number of live cells was observed as mixed bacterial population stained green was visible at both the tested concentrations. VAN had little effect on 24 h biofilm at $10×MIC_b$ where no distinction between control biofilm and VAN treated biofilms were visible. Only at $20×MIC_b$ of VAN, slight decrease in the height of mature biofilm was observed (FIGS. 7B.f and 7B.g). The confocal imaging experiments were repeated three times on three different days and similar results were obtained (representative data of one set is shown here).

Example 11

Serum Stability Assay

To determine activity of designed peptidomimetics in physiological fluids serum stability was evaluated using a standard reverse phase HPLC method as described previously with slight modifications [*Antimicrob. Agents Chemother.*, 54: 4003-4005, 2010]. Towards this the peptidomimetics were dissolved in pre-warmed 25% v/v human serum in 0.1M phosphate buffer saline (150 mM NaCl, pH 7.2) at final concentrations of 150 μg/ml and incubated at 37° C. At fixed time interval (0, 4, 24, 48, and 72 h) aliquots of 1004 incubation mixture were withdrawn in duplicates. The mixture was precipitated with a mixture of acetonitrile, water, and formic acid (300 μl; 89:10:1 by volume) on ice. After 45 min on ice, the samples were centrifuged (10 min, 12,000 g, at 4° C.) and the supernatants were analyzed by RP-HPLC with UV detection at 220 nm using the same column and data system as described above for characterization. The results demonstrated >85% intact peptidomimetics even after 72 h of incubation.

We claim:
1. Novel N-terminally modified branched polyamine conjugated peptidomimetics of the following structure:

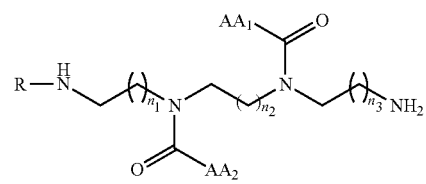

where, $n_1 = n_2 = n_3 = 1, 2, 3, 4$ wherein, R is hydrogen or a carboxylicacid moiety conjugated through amide bond (—CONH—)selected from 2-(4-(trifluoromethyl) phenyl) acetic acid, 2-(4-fluorophenyl) acetic acid, 4-(aminomethyl) benzoic acid, 3-(4-hydroxyphenyl)propanoic acid, 3-(3,4-dihydroxyphenyl)propanoic acid, 3-(3,4dihydroxyphenyl) acrylic acid, (E)-3-(4-hydroxyphenyl)acrylic acid, (2E)-3-Phenylprop-2-enoic acid, cinnamic acid, [1,1'-biphenyl]-4-carboxylic acid, [1,1':4',1"-terphenyl]-4-carboxylic acid, [1,1':4',1"-terphenyl]-2-carboxylic acid, 2-naphthoic acid, 2-(naphthalen-2-yl)acetic acid or an aliphatic acid moiety conjugated through amide bond (—CONH—) selected from

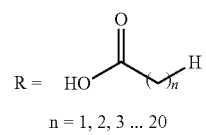

$n = 1, 2, 3 ... 20$ or an unsaturated fatty acid selected from oleic acid, linoleic acid or linolenic acid, wherein, AA1 and AA2 are amino acids selected from tryptophan (W), Ornithine (O), lysine (K) or phenylalanine (F).

2. The peptidomimetics as claimed in claim 1 wherein the peptidomimetics have properties of being antimicrobial agents against susceptible as well as MDR bacterial strains.

3. A method of treating microbial infections in mammals using a therapeutically effective amount of the peptidomimetics of claim 1.

4. The methods of claim 3, wherein the microbial infection is a bacterial infection caused by planktonic or bacteria of bacterial biofilms.

5. The methods of claim 4, wherein the microbial infection is a bacterial infection caused by MDR bacteria of planktonic or sessile forms (biofilms).

6. The method of claim 5, wherein the bacterial infection caused by bacteria selected from the staphylococcus species.

7. The method of claim 6, wherein the bacterial infection is caused by MRSA.

8. The composition comprising of any of the peptidomimetics as claimed in claim 1 and a pharmaceutically acceptable drug delivery vehicle.

9. The composition as claimed in claim 8 in the form of emulsions, liquids, cream, ointment or paste.

10. The composition comprising of any of the peptidomimetics as claimed in claim 1 useful for treatment of skin infections, systemic infections, burns or wounds healing in humans or animals.

* * * * *